US005552293A

United States Patent [19]
Lindholm et al.

[11] Patent Number: 5,552,293
[45] Date of Patent: Sep. 3, 1996

[54] TUMOR ANTIGEN SPECIFIC ANTIBODY

[75] Inventors: Leif G. Lindholm, Kullavik; Jan Holmgren, Vastra Frolunda; Peter Lind, Uppsala, all of Sweden

[73] Assignee: Pharmacia Aktiebolag, Uppsala, Sweden

[21] Appl. No.: 438,123

[22] Filed: May 8, 1995

Related U.S. Application Data

[63] Continuation of Ser. No. 906,350, Jul. 2, 1992, abandoned.

[30]    Foreign Application Priority Data

Jul. 3, 1991 [SE] Sweden .................................. 9102074

[51] Int. Cl.$^6$ ......................... G01N 33/53; G01N 33/574
[52] U.S. Cl. .................................... 435/7.23; 435/240.27; 436/64; 436/512; 530/388.8; 530/388.85; 530/387.7
[58] Field of Search ............................. 435/7.23, 240.27; 436/64, 813, 512; 530/388.8, 388.85, 387.7

[56]           References Cited

U.S. PATENT DOCUMENTS

| 4,752,569 | 6/1988 | Terasaki et al. ..................... 435/240.27 |
| 4,904,596 | 2/1990 | Hakomori .......................... 435/240.27 |

FOREIGN PATENT DOCUMENTS

| WO90/05306 | 5/1990 | WIPO . |
| WO92/01470 | of 1992 | WIPO . |
| WO92/01474 | 1/1992 | WIPO . |

OTHER PUBLICATIONS

Neuberger TIBS pp. 347–349 (Sep. 1985) "Making novel antibodies by expressing transfected immunoglobulin genes".

Goldenberg et al. "In-vivo antibody imaging for the defection of human tumors" In *Cancer Imaging with Radio labeled Antibodies* pp. 273–292, Goldenberg (ed) 1990 Kluwer Academic Publishers.

Waldmann Science 252 pp. 1657–1662 (21 Jun. 1991) "Monoclonal Antibodies in Diagnosis and Therapy".

Caton, et al. "Structural and Functional implications of a Restricted Antibody Response to a Defined Antigenic Region on the Influenza Virus Hemagglutinin", *The EMBO Journal*, (1986) vol. 5, No. 7, pp. 1577–1587.

Haglund, G. et al. "Tissue Expression of the Tumour Associated Antigen CA242 in Benign and Malignant Pancreatic Lesions. A Comparison with CA 50 and CA 19–9", *Br. J. Cancer*, 60, (1989) 845–851.

Larson, L. N. et al. "Mouse Monoclonal Antibodies for Experimental Immunotherapy Promotes Killing of Tumor Cells", *Int. J. Cancer*, 42, (1988) 877–882.

Johansson, C. et al. "Comparison of Serological Expression of Different Epitopes on the CA50–Carrying Antigen CanAg", *Int. J. Cancer*, 48, (1991) 757–763.

Kuusela, P. et al. "Comparison of a New Tumour Marker CA 242 with CA 19–9, CA 50 and Carcinoembryonic Antigen (CEA) in Digestive Tract Diseases", *Br. J. Cancer*, 63, (1991) 636–640.

Sell, S. "Cancer–Associated Carbohydrates Identified by Monoclonal Antibodies", *Human Pathology*, 10(21), (1990) 1003–1019.

Baeckstrom, D. et al. "Purification and Characterization of a Membrane–bound and a Secreted Mucin–type Glycoprotein Carrying the Carcinoma–associated Sialyl-Le$^a$ Epitope on Distinct Core Proteins*", *J. Biol. Chem.*, 266(32), (1991), 21537–21547.

Debinski, W. et al. "Monoclonal Antibody C242–Pseudomonas Exotoxin A: A Specific and Potent Immunotoxic with Antitumor Activity on a Human Colon Xenograft in Nude Mice", *Clinical Research*, 40(2), (1992) 211A.

Dohlsten, M. et al. "Monoclonal Antibody–Targeted Superantigens: A Different Class of Anti Tumor Agents", *Proc. Natl. Acad. Sci., USA*, 88 (1991) 9287–9292.

Finan, P. J. et al. "An Evaluation of Ca 242 as a Marker in Gastointestinal Cancer", 15th International Cancer Congress, Hamburg, Germany, Aug. 16–22, 1990, *J. Cancer Res. Clin. Oncol.*, 116 (Suppl. Part 1), (1990) 255.

Gretarsdottir, J. et al. "Comparison of Three Monoclonal Antibodies fo Immunoscintigraphy of Human Colon Carcinoma in Nude Mice", Meeting on Advances in the Applications of Monoclonal Antibodies in Clinical Onocology, London England, May 28–30, 1986, *Br. J. Cancer*, 54(3) (1986) 553–554.

Habib, N. A. et al. "Evaluation of Therapeutic Use of Radioactive Monoclonal Antibodies C242 and C215 in Transplanted Murine Tumours", *European Journal of Surgical Onocology*, 15 (1989) 367–370.

Habib, N. A. et al. "Evaluation of the Therapeutic Use of Radioactive Monoclonal Antibody C242 in Transplanted Murine Mammary Tumours", XVTH Annual Meeting of the International Society for Oncodevelopmental Biology and Medicine, Quebec, Canada, Aug.30–Sep. 3, 1987, *Tumor-–Biol.*, 8(6) (1988) 357.

Nilsson, O. et al. "Sensitivity and Specificity of CA242 in Gastr–intestinal Cancer. A Comparison with CEA, CA50 and CA 19–9", *Br. J. Cancer*, 65, (1992) 215–221.

Ouyang, Qin et al. "CEA and Carbohydrate Antigens in Normal and Neoplastic Colon Mucosa", *Acta Path. Microbiol. Immunol. Scand. Sect. A*, 95, (1987) 177–183.

Pasanen, P. A. "Clinical Evaluation of a New Serum Tumour Marker CA242 in Pancreatic Carcinoma", *Br. J. Cancer, l 65 (1992) 731–734.*

(List continued on next page.)

*Primary Examiner*—Toni R. Scheiner
*Attorney, Agent, or Firm*—Lowe, Price, LeBlanc & Becker

[57]            ABSTRACT

A monoclonal antibody that reacts with the CA-242 antigen is provided. The antibody can be obtained by culturing the hybridoma cell line C242:II with the ECACC identification number 90012601, or an artificial or spontaneous mutant thereof. Cell lines producing the antibody are also provided. The antibody is useful for therapeutic and diagnostic purposes.

9 Claims, 4 Drawing Sheets

OTHER PUBLICATIONS

Pujol, J. L. et al. "Pilot Study of Serum CA 242 as a Tumor Marker of Non–Small Cell Lung Cancer NSCLC", 1991 International Conference of the American Lung Association and the American Thoracic Society, Anaheim California, USA, May 12–15, *Am. Rev. Respir. Dis.*, 143 (4 Part 2) (1991) A202.

Rothnie, N. et al. "Monoclonal–Antibody C242 Recognizes a Tumor Associated Antigen in Colorectal Carcinomas", Meeting Abstract, The British Society of Gastroenterology, *Gut*, 31(5) (1990) A619.

Hill, J. et al. "Do Measured Parameters of Blood Clotting Help Predict Haemorrhage After Endoscopic Sphincterotomy?", Meeting Abstract, The British Society of Gastroenterology, *Gut*, 31(5), (1990) A608.

Seidegard, J. et al. "Pharmacokinetics of Internally Labelled and Iodinated Monoclonal Antibodies C215 and C242 in the Rat and Mouse", 7th International Meeting in Clinical Oncology, London, England, UK, May 14–16, 1990, Monoclonal Antibodies in Clinical Oncology, *Eur. J. Cancer*, 26(9), (1990) 1017.

Sell, S. "Cancer Carbohydrates Identified by Monoclonal Antibodies", *J. Tumor Marker Oncology*, 5(3) (1990) 209.

Seveus, L. et al. "Time–Resolved Fluoresence Imaging of Europium Chelate Label in Immunohistochemistry and In Situ Hybridization", *Cytometry*, 13 (1992) 329–338.

Dahlen, U. et al. "Development of Seriological Assay for Simultaneous Determination of CEA and CA242 Using Separate Solid–Phases", I.A.T.M.O. 19–23 Sep. 1988.

Dahlen, U. et al. "Development of Seriological Assay for Simultaneous Determination of CEA and CA–242 Using Separate Solid–Phases", ISO BM 25–29 Sep. 1988.

Haglund, C. et al. "Tumor Associated Antigen CA–242 in Pancreatic Cancer", I.A.T.M.O. Stockholm 1988.

Haglund, C. et al. "CA–242 as a Tumor–Marker in Pancreatic Cancer", I.A.T.M.O. Stockholm 19–23 Sep. 1988.

Johansson, C. et al. "New Serological Human Carcinoma Markers, and Their Association ith the Molecule Which Carries the CA50 Carbohydrate Antigen (SiLe$^a$ and SiLactotetraose)", ISO BM, Paris 1985.

Johansson, C. et al. "A New Antibody Combination of C50 and C–242 MABs Increases the Tumor Specifict6y of the Delfia Assay for Detection of the Cancer–Assocaited, CanAg Antigen", International Symposium on the Clinical Applications of Monoclonal Antibodies, Guildford, Surrey, UK, 1987.

Kuusela, P. et al. "A New Tumor Marker CA–242, In Gastrointestinal Diseases, XVI International ISO BM Congress 25–29 Sep. 1988," Barcelona.

Forssell Aronsson, E. et al. "Comparison of Seven Iodine–Lagelled Monoclonal Antibodies in Nude Mice with Human Colon Carcinoma Xenografts", *Acta Oncologia*, 30(3) (1991) 385–393.

Johansson, C. et al. "New Serological Human Carcinoma Markers, and Their Association with the Molecule Which Carries the CA50 Carbohydrate Antigens (SiLe$^a$ and SiLactotetraose)", Brochure or Poster from Stena Diagnostics, Before 1987.

Johansson, C. et al. "A New Antibody Combination in C50 and C242 MABS Increase the Tumor Specificity of the Delfia Assay for Detection of the Cancer–Associated, CanAg Antigen", Brochure or Poster from Stena Diagnostics, Before 1987.

Lindholm, L. et al. "An Immunoradiometric Assay (IRMA) for the CA–50 Antigen", *Tumor Marker Antigens*, ed. J. Holmgren, Studentlitteratur, Lund, 1985.

Walz, G. et al. "Recognition of ELAM–1 of the Sialyl–Le$^x$ Determinant on Myeloid and Tumor Cells", *Science*, 250 (1990) 1132–1135.

Chia, D. et al. "Use of Monoclonal Antibodies to Sialylated Lewis$^x$ and Sialylated Lewis$^a$ for Serological Tests of Cancer", *Cancer Research*, 45 (1985) 435–437.

Yuan, M. et al. "Expression of Lewis$^x$ and Sialylated Lewis$^x$ Antigens in Human Colorectal Polyps", *J. National Cancer Institute*, 78(5) (1987) 479–488.

Berg, E. et al. "Communication: A Carbohydrate Domain Common to Both Sialyl Le$^a$ and Sialyl Le$^x$ is Recognized by the Endothelial Cell Leukocyte Adhesion Molecule ELAM–1*", *J. Biol. Chem.* 266(23) (1991) 14869–14872.

Itai, S. et al. "Significance of 2–3 and 2–6 Sialylation of Lewis A Antiven in Pancrease Cancer", *Cancer*, 61 (1988) 775–787.

Figure 3

```
     GGAATTCGGCACGAGGAGTTTTTTTGTATCAAGTTCTCAGAATGAGGTGCCTAGCTGAGT
  1  ---------+---------+---------+---------+---------+---------+  60
                                                 MetArgCysLeuAlaGluPhe  -

TCCTGGGGCTGCTTGTGCTCTGGATCCCTGGAGCCATTGGGGATATTGTGATGACTCAGG
 61  ---------+---------+---------+---------+---------+---------+ 120
       LeuGlyLeuLeuValLeuTrpIleProGlyAlaIleGlyAspIleValMetThrGlnAla -
                                         ⊥ VK →

CTGCACCCTCTGTACCTGTCACTCCTGGAGAGTCAGTATCCATCTCCTGCAGGTCTAGTA
121  ---------+---------+---------+---------+---------+---------+ 180
       AlaProSerValProValThrProGlyGluSerValSerIleSerCysArgSerSerLys -
                                                         CDR1

AGAGTCTCCTGCATAGTAATGGCAACACTTACTTGTATTGGTTCCTGCAGAGGCCAGGCC
181  ---------+---------+---------+---------+---------+---------+ 240
       SerLeuLeuHisSerAsnGlyAsnThrTyrLeuTyrTrpPheLeuGlnArgProGlyGln -
                       CDR1

AGTCTCCTCAGCTCCTGATATATCGGATGTCCAACCTTGTCTCAGGAGTCCCAGACAGGT
241  ---------+---------+---------+---------+---------+---------+ 300
       SerProGlnLeuLeuIleTyrArgMetSerAsnLeuValSerGlyValProAspArgPhe -
                            CDR2

TCAGTGGCAGTGGGTCAGGAACTGCTTTCACACTGAGAATCAGTAGAGTGGAGGCTGAGG
301  ---------+---------+---------+---------+---------+---------+ 360
       SerGlySerGlySerGlyThrAlaPheThrLeuArgIleSerArgValGluAlaGluAsp -

ATGTGGGTGTTTATTACTGTCTGCAACATCTAGAGTATCCGTTCACGTTCGGTCCTGGGA
361  ---------+---------+---------+---------+---------+---------+ 420
       ValGlyValTyrTyrCysLeuGlnHisLeuGluTyrProPheThrPheGlyProGlyThr -
                        CDR3

CCAAGCTGGAGCTGAAACGGGCTGATGCTGCACCAACTGTAACG
421  ---------+---------+---------+---------+---- 464
       LysLeuGluLeuLysArgAlaAspAlaAlaProThrValThr -
          ← VK ⊥ CK →
```

FIGURE 4

```
    GAATTCGGCACGAGATTGAGCCCAAGTCTTAGACATCATGGATTGGCTGCGGAACTTGCT
1---------+---------+---------+---------+---------+---------+
                                         MetAspTrpLeuArgAsnLeuLeu

ATTCCTGATGGCAGCTGCCCAAAGTATCCAAGCACAGGTCCAGTTGGTGCAGTCTGGACC
61--------+---------+---------+---------+---------+---------+
    PheLeuMetAlaAlaAlaGlnSerIleGlnAlaGlnValGlnLeuValGlnSerGlyPro
                                        ⌐ VH →

TGAGCTGAAGAAGCCTGGAGAGACAGTCAAGATCTCCTGCAAGGCTTCTGATTATACCTT
121-------+---------+---------+---------+---------+---------+
    GluLeuLysLysProGlyGluThrValLysIleSerCysLysAlaSerAspTyrThrPhe

CACATACTATGGAATGAACTGGGTGAAGCAGGCTCCGGGAAAGGGTTTAAAGTGGATGGG
181-------+---------+---------+---------+---------+---------+
    ThrTyrTyrGlyMetAsnTrpValLysGlnAlaProGlyLysGlyLeuLysTrpMetGly
            CDR1

CTGGATAGACACCACCACTGGAGAGCCAACATATGCTGAAGATTTTAAGGGACGGATTGC
241-------+---------+---------+---------+---------+---------+
    TrpIleAspThrThrThrGlyGluProThrTyrAlaGluAspPheLysGlyArgIleAla
                           CDR2

CTTCTCTTTGGAGACCTCTGCCAGCACTGCCTATTTGCAGATCAAAAACCTCAAAAATGA
301-------+---------+---------+---------+---------+---------+
    PheSerLeuGluThrSerAlaSerThrAlaTyrLeuGlnIleLysAsnLeuLysAsnGlu

GGACACGGCTACATATTTCTGTGCAAGACGGGGGCCTTACAACTGGTACTTTGATGTCTG
361-------+---------+---------+---------+---------+---------+
    AspThrAlaThrTyrPheCysAlaArgArgGlyProTyrAsnTrpTyrPheAspValTrp
                              CDR3

GGGCGCAGGGACCACGGTCACCGTCTCCTCAGCCAAAACGACNCCCCcaTCTGTCTATCC
421-------+---------+---------+---------+---------+---------+
    GlyAlaGlyThrThrValThrValSerSerAlaLysThrThrProProSerValTyrPro
                                        ← VH ⌐ CH1 →
```

TUMOR ANTIGEN SPECIFIC ANTIBODY

This application is a continuation of application Ser. No. 07/906,350 filed Jul. 2, 1992, now abandoned.

The present invention relates to a novel monoclonal tumour antigen specific antibody, a cell line which produces the antibody, a pharmaceutical composition comprising the monoclonal antibody, and the use of the antibody in diagnosis and therapy, and the use of the cell line for the production of the antibody.

The hybridoma technology for the production of monoclonal antibodies, which was first described by Köhler and Milstein (Nature, 256, 495–497, 1975), is nowadays well established. By this technology myeloma cells are fused to lymphocytes from animals which have been immunized with a particular antigen. The resulting hybridoma cell produces antibodies specific against a single antigenic determinant. Monoclonal antibodies have therefore to a large extent begun to replace conventional antisera in diagnostic standard kits for immunoassays. Significant research has also been done to adapt hybridoma technology for therapeutic purposes.

It is further well-known that the transformation of normal tissue cells to tumour cells is associated with a change of the carbohydrate structure on the cell surface. Many carbohydrate structures serve as antigens, and the tumour-modified structures represent a type of so-called tumour-associated antigens (abbreviated TAA). The cell surface carbohydrate structures are linked to either a lipid moiety, in which case they are called glycolipids, or to proteins or peptides, in which case they are called glycoproteins or glycopeptides, respectively. A common designation for the two forms is glycoconjugate.

Tumour-associated glycoconjugate antigens are previously known in relation to human tumour diseases. Thus, two carcinoma associated antigens, CEA (carcinoma embryonal antigen) and GICA (gastrointestinal cancer antigen) carrying the epitope CA 19-9 have been demonstrated particularly in gastrointestinal carcinomas, while another third epitope, CA-50, seems to be a general carcinoma antigen. All these antigens are secreted from the tumour cell surface and can be demonstrated in blood serum. These discoveries have urged the search for monoclonal antibodies which recognize tumour-specific antigens and which may be used in the immunolocalization and immunotherapy of various cancer diseases.

Monoclonal antibodies having pancreatic and colorectal cancer specificity are mentioned in several prior publications and conference abstracts under the designation C242 (corresponding antigen CA-242); see e.g. Larsson L. N. et al., Int. J. Cancer 42 (1988) 877–882, Lindholm L et al., "An Immunoradiometric Assay (IRMA) for the CA-50 antigen", Tumor Marker Antigens, Ed Jan Holmgren, Studentlitteratur 1985, Haglund C. et al., Br. J. Cancer 60 (1989) 845–51, Sell S., Human Pathology 21:10 (1990) 1003–19, Johansson C. et al., Int. J. Cancer 48 (1991) 757–763, and Kuusela P. et al., Br. J. Cancer 63 (1991) 636–40. Such C242 antibody has, however, never been disclosed previously more specifically or to such an extent that it could be produced by a person skilled in the art, and it has hitherto never been publicly available.

The present invention thus relates to a novel monoclonal antibody having significant specificity for gastrointestinal, in particular pancreatic and colorectal, cancer cells, a specific such monoclonal antibody being that which hereinafter is designated as C242:II.

C242:II is a monoclonal murine antibody of IgG class produced when culturing in an appropriate medium a hybridoma cell line obtained by fusing spleen cells from a mouse, which has been immunized with a human colonic adenocarcinoma cell line, with the murine myeloma cell line Sp2/0, as will be described in more detail in Example 1 below. A hybridoma cell line producing the C242:II antibody was deposited on Jan. 26, 1990 in accordance with the Budapest Treaty at the European Collection of Animal Cell Cultures (ECACC), PHLS Centre for Applied Microbiology and Research, Porton Down, Salisbury Wilts., U.K., where it obtained the depository accession number 90012601. Reference to this deposit has been made in our copending international patent application PCT/SE91/00496 (WO-A-9201470) that has priority from Jul. 20, 1990.

In one aspect the present invention provides a novel monoclonal antibody which is the monoclonal antibody C242:II or an antibody having substantially the same properties, i.e. a functional equivalent, hereinafter commonly referred to as "antibody according to the invention".

In a further aspect the invention provides a cell line capable of producing the antibody according to the invention, particularly the above mentioned deposited hybridoma cell line 90012601.

By the expressions "substantially the same properties" and "functional equivalent" is meant that the antibody should have at least substantially the same immunologic specificity as that produced by the deposited cell line 90012601, i.e. bind to the same antigenic determinant or epitope, and compete with the C242:II antibody for binding at that site.

Within the scope of the expression "antibody according to the invention" is also intended to be comprised antigen binding fragments of the antibody. Such fragments will retain the binding capability and specificity of the unfragmented immunoglobulin and may, for example, be obtained by degrading the antibody by proteolytic enzymes, such as pepsin. The latter gives rise to a $F(ab')_2$ molecule and smaller peptides, the $F(ab')_2$ part being an example of such an antigen binding fragment. Also comprised are corresponding antibodies or fragments produced by genetic engineering as well as derivatized or humanized forms of the antibody. Comprised within the inventive concept are antibodies deriving from mouse and other animals and of different Ig classes/subclasses having the same specificity. With respect to antibody-active fragments and recombinantly produced variants, the class/subclass of an antibody according to the invention may become less important because the unique class/subclass specific determinants may be more or less omitted in the constructs. Thus the inventive concept spans from fully non-human to fully human antibodies and includes different chimeric forms. Fully human antibodies may be obtained by culturing immortalized human antibody producing cells.

A certain aspect of the invention comprises antibodies that have a binding affinity/avidity for the CA-242 antigen/epitope which is up to $10^{+1}$ times, and in some cases down to $10^{-1}$ times, the binding affinity/avidity of the antibody produced by the deposited hybridoma cell line. The cross-reactivity in question is measured by blocking/binding assays as normally contemplated within the field. These affinity/avidity ranges apply in particular to unfragmented and underivatized non-human antibodies.

With respect to genetic engineering as mentioned above, the cDNA's of the variable regions of the light and heavy chains of the C242:II monoclonal antibody were cloned as will be described further in Example 4 below. Before discussing this in any more detail it may not be out of place to give a brief general description of the basic immunoglobulin structural unit, reference being made to FIG. 1 of the accompanying drawings which describes the general structure of an antibody, i.e. immunoglobulin, of class G.

Referring to FIG. 1, the immunoglobulin consists of two identical light (L) polypeptide chains and two identical heavy polypeptide chains (H), the four chains being joined by disulphide bonds and various non-covalent forces in a symmetric "Y"-configuration. Each heavy chain has a variable domain ($V_H$) at each end followed by a number of constant domains ($C_H$), and each light chain has a variable domain ($V_L$) at one end and a constant domain ($C_L$) at the other end. There are two types of light chains, designated kappa and lambda, respectively. The variable domain of the light chain is aligned with the variable domain of the heavy chain, and the costant domain of the light chain is aligned with the first constant domain of the heavy chain, the variable domains of the light and heavy chains forming the antigen binding site.

The variable domains of the light and heavy chains have the same general structure, each comprising three hypervariable regions, called complementarity determining regions, or CDR's, intervening between four framework regions, or FR's. The CDR's of each variable domain are kept in close proximity by the framework regions, and the two sets of CDR's together provide for the specificity of the antibody.

In order to clone the cDNA's of the variable portions of the light and heavy chains of the C242:II antibody, a cDNA phage library was first prepared from the C242:II hybridoma by per se known methods. Hybridization probes covering constant parts of the heavy chain and the kappa light chain, respectively, were then prepared from mouse genomic DNA using the polymerase chain reaction (PCR) and suitable primers. The resulting probes were used to screen the cDNA library for cDNA clones containing DNA sequences encoding the heavy and kappa chains of the C242:II antibody. Positively hybridizing phage clones were expanded and the cDNA was excised in the form of plasmids. The latter were characterized by restriction enzyme mapping, and plasmids containing inserts of the expected sizes were sequenced. In order to determine the CDR regions, the amino acid sequences encoded by the sequenced inserts were compared with those of previously known mouse kappa and heavy chains, considering the basic locations of CDR regions as defined by, e.g., Kabat E. A., et al. (1987), Sequences of Proteins of Immunological Interest, 4th Ed., U.S. Department of Health and Human Services, National Institutes of Health. It was found that the CDR's of the respective chains had the following amino acid sequences (as are also shown in FIGS. 3 and 4 of the accompanying drawings):

---
Kappa chain/Light chain

CDR1:
ArgSerSerLysSerLeuLeuHisSerAsnGlyAsnThrTyrLeuTyr(TrpPhe)
CDR2:
ArgMetSerAsnLeuValSer(GlyVal)
CDR3:
LeuGlnHisLeuGluTyrProPheThr(PheGly)

Heavy chain

CDR1:
(PheThr)TyrTyrGlyMetAsn
CDR2:
(MetGly)TrpIleAspThrThrThrGlyGluProThrTyrAlaGluAspPhe-
Lys
Gly(ArgIle)
CDR3:
(AlaArg)ArgGlyProTyrAsnTrpTyrPheAspVal(TrpGly)

---

The terminal dipeptide residues within brackets are optional variations of the CDR sequences. The kappa chain in FIG. 3 contains a cys residue meaning that the amino-terminal limits of its CDRs are well-defined.

The DNA sequences encoding the above CDR's are illustrated in FIG. 4. With the knowledge of these CDR amino acid and/or DNA sequences the skilled person may introduce the CDR regions of the C242:II antibody into the cloned variable parts of another antibody or antibody fragment by means of site-directed mutagenesis as is per se known in the art. Such procedure, generally known as "CDR grafting", involves substitution at DNA level of the CDR encoding sequences of the C242:II antibody for the CDR encoding sequences of the recipient antibody or fragment and will result in an antibody or antibody fragment having a corresponding specificity as the C242:II monoclonal antibody. Included within the scope of the antibody according to the invention is therefore, of course, any antibody or antibody fragment comprising the above defined CDR's or alternative CDR amino acid sequences that grafted onto functional antibody framework regions cross react with the antibody produced by the deposited hybridoma cell line ECACC 90012601.

The antibody according to the invention is directed against a tumour associated antigen, designated herein as CA-242, which appears to be a sialylated carbohydrate antigen expressed en the same macromolecule as the antigen CA-50 mentioned above. Structurally, this antigen differs from the CA-50 epitope in that the antibody according to the invention does not react with either sialylated Lewis-a substance or sialosyllacto-N-tetraose. A monoclonal antibody against CA-50 can, however, inhibit the binding of the antibody according to the invention to CA-50, suggesting a structural relation between CA-50 and the antigen recognized by the antibody according to the invention. The tumour-associated antigen CA-242 is expressed in the vast majority of colo-rectal tumours and is only weakly expressed or absent in normal colonic tissue.

Following binding to cellbound antigen of the antibody according to the invention, the antigen-antibody complex so formed is capable of being endocytosed or internalized into the cells. This is a prominent property of the C242:II antibody as deposited.

Although the antigen recognized by the antibody according to the invention is very poorly expressed in normal pancreatic and colonic tissue, it is strongly expressed in pancreatic carcinoma and colonic adenocarcinoma cells. The antibody according to the invention would therefore find use in immunolocalization as well as therapy of human pancreatic cancer and human colonic carcinoma.

In still another aspect the present invention thus provides the use of the novel antibody according to the invention in immunoassay or therapy.

In a further aspect the present invention provides a pharmaceutical composition comprising the novel antibody according to the invention.

An immunoassay for in vitro testing based upon the novel antibody according to the invention may be designed in accordance with per se conventional immunological techniques in the art, utilizing the antibody according to the invention in a labelled or unlabelled form and determining the complex formation of the antibody with specific antigenic species in the sample to be tested. In the first case the antibody may be labelled with a detectable label, such as a radiolabel, a chemiluminiscer, a fluorescer or an enzyme label, whereas in the latter case the antibody is detected via a complex formed with a labelled substance or by non-labelling techniques, such as biosensor methods, e.g. based upon surface plasmon resonance. The sample may, for example, be in the form of a body fluid, such as serum, or a tissue preparation (histochemical assay).

For in vivo diagnostic purposes the antibody according to the invention is provided with a suitable externally detectable label, such as e.g. a radiolabel or a heavy metal atom, and administered to a subject whereupon the possible localized accumulation of antibody in the body is determined.

For therapeutical use the novel antibody according to the invention may be formulated in a variety of pharmaceutical compositions and preparations with pharmaceutically acceptable carriers, such as e.g. water, and be administered in various conventional ways, e.g. intravenously, subcutaneously, intramuscularly or intraperitoneally.

In the following non-limiting examples the preparation of a hybridoma producing the novel antibody according to the invention will be described, the use thereof in immunohistological evaluation, endocytosis thereof, and the cloning of cDNA's encoding the light and heavy chains of the C242:II monoclonal antibody. Reference will be made to the accompanying drawings wherein:

BRIEF DESCRIPTION OF THE FIGURES

FIG. 3 is a representation of the detailed cDNA sequence encoding the variable domain of the kappa chain of the C242:II monoclonal antibody along with the corresponding amino acid sequence; and FIG. 4 is a representation of the detailed cDNA sequence encoding the variable domain of the heavy chain of the C242:II monoclonal antibody along with the corresponding amino acid sequence.

EXAMPLE 1

Figure 1:
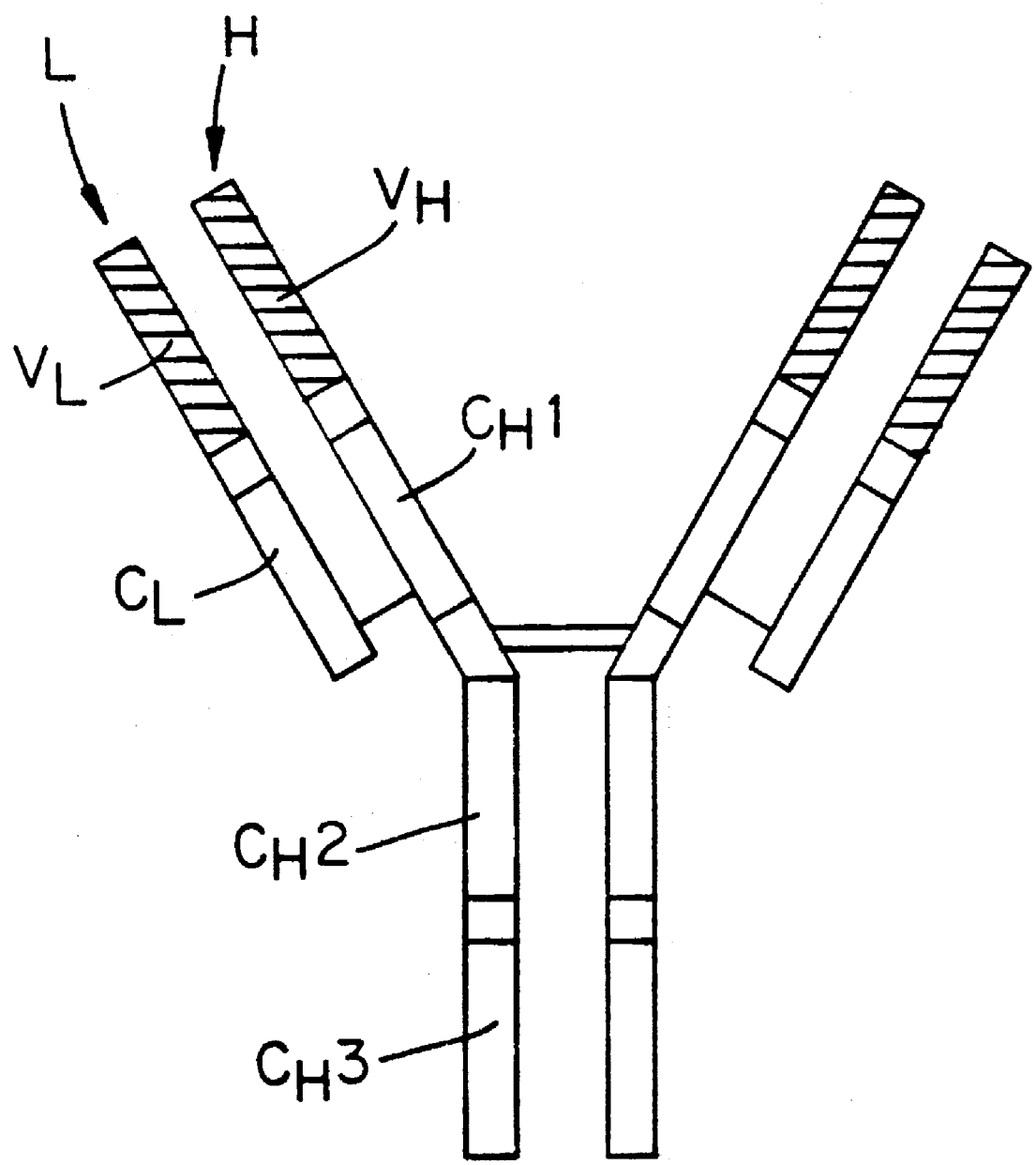
FIG. 1 is a schematic representaion of the general immunoglobulin G structure.
Figure 2:
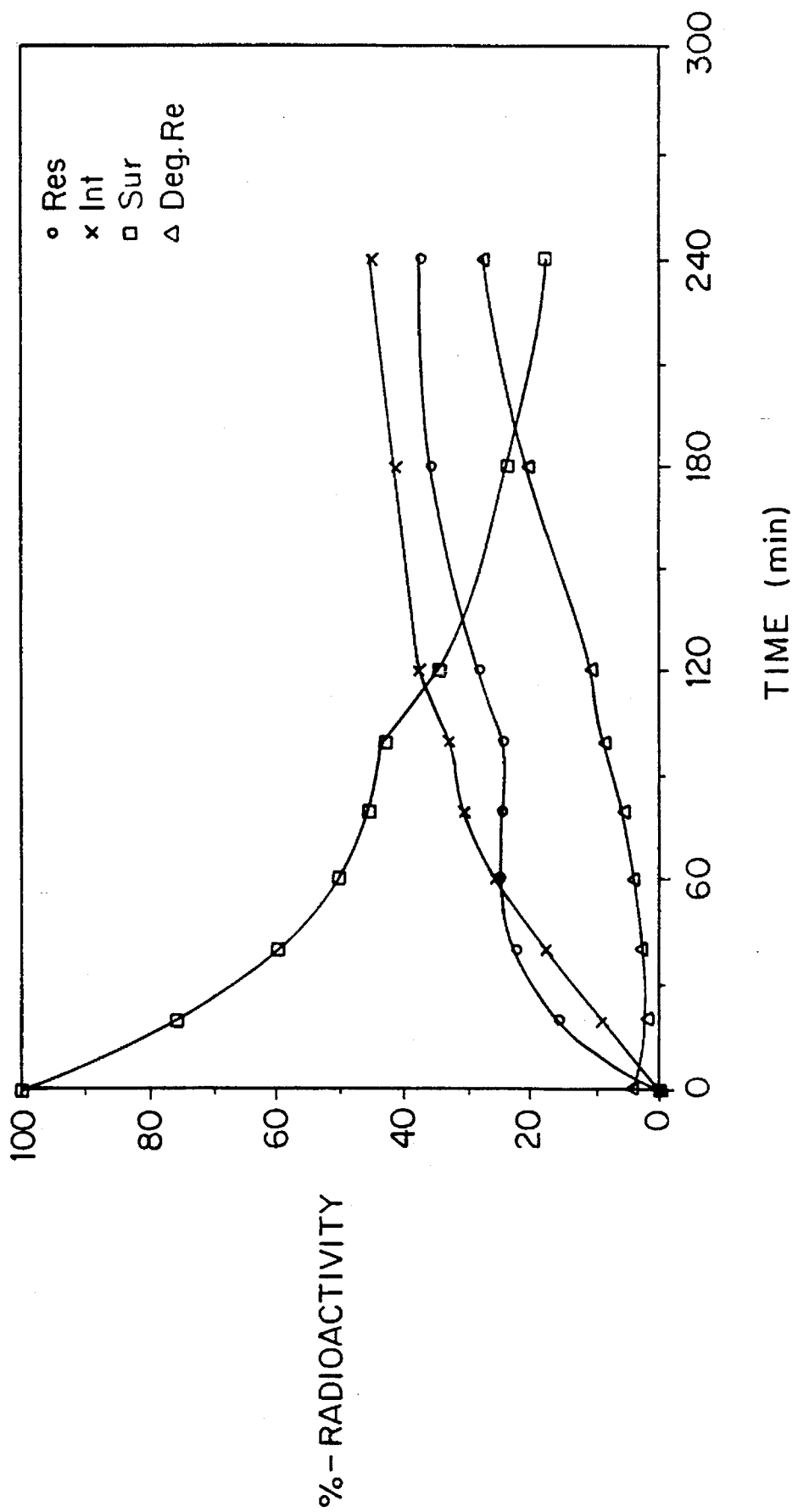
FIG. 2 is a graph showing the endocytosis of C242:II cells.

Establishment of hybridoma cell line and production of C242:II

Preparation of established spleen cells

A human colorectal carcinoma cell line, COLO 205, commercially obtainable from the American Type Culture Collection (ATCC), Rockville, Md., U.S.A., under the accession No. CCL 222, was routinely cultered in Iscove's MEM complemented with 10% fetal calf serum (FCS). Cells were harvested prior to confluence, normally 2 to 3 days after subcultivation, and washed 3 times with phosphate buffered saline (PBS) for immunization.

BALB/c mice, 4 to 6 weeks old, were immunized intraperitoneally with a priming dose of $3 \times 10^7$ COLO 205 cells suspended in 0.1 ml of PBS. The animals were then boosted with another 0.1 ml suspension of $3 \times 10^7$ COLO 205 cells and sacrificed four days later and the spleens were removed. The spleens were then dissociated into a single cell suspension.

Preparation of hybridoma $1.2 \times 10^8$ spleen cells from the above described cell suspension were distributed among two tubes. To each tube were additionally added $10^8$ myeloma cells from the mouse myeloma cell line Sp2/0 (available from the collection of American Type Culture Collection (ATCC), Rockville, Md., U.S.A. under the accession No. CRL 1581). The two tubes were centrifuged, and all liquid was decanted. To each tube were then slowly added 2 ml of 37° C. PEG solution (10 g of PEG $M_W$ 4000, 1 ml of DMSO and 10 ml of monoclonal saline) over 1 minute and with constant stirring. The tubes were transferred to a water-bath at 37° C. for 90 seconds with gentle stirring. The fusion was interrupted by adding to each test tube a physiological buffer solution according to the following scheme: 2 ml during the first 30 seconds, 6 ml during the following 30 seconds and another 32 ml over 1 minute. After washing of the cell suspension in culture medium it was suspended in totally 100 ml of hypoxanthine/aminopterin/thymidine (HAT) supplemented culture medium. The culture medium was Iscove's MEM supplemented with 10% FCS, L-asparagine (36 mg/l), L-arginine-HCl (116 mg/l), folic acid (10 mg/l), L-glutamine (292.3 mg/l), sodium pyruvate (110.1 mg/l) and mercaptoethanol (3.49 µl/l). Aliquotes of 50 µl were distributed to the wells of 96-well tissue culture dishes. The wells had been pre-coated with 250 µl of macrophage suspension from BALB/c mice ($2 \times 10^4$ cells/ml) in HAT supplemented culture medium. Medium was changed 6 days after fusion.

Screening of antibody secreting hybridomas

The spent medium from day 6 above was tested for COLO 205 positive antibodies as described by Kennett R. H., "Enzyme-linked antibody assay with cells attached to polyvinyl chloride plates". Monoclonal Antibodies. Hybridomas. A new dimension in biological analyses. Eds. H. R. Kennett, T. J. McKevin, K. B. Bechtol, Plenum Press, New York 1980. In brief, the wells of Nunc immunoplates type IIF were coated with $2 \times 10^5$ cells/well of COLO 205 cells (1 mg/100 ml PBS); coating volume 50 µl. The above mentioned spent culture medium from day 6 was then added to the coated wells, 50 µl/well. After incubation over night at room temperature peroxidase conjugated anti-mouse Ig (Dakopatts P260, Dakopatts A/S, Copenhagen, Denmark) diluted (1/500) in 1% BSA-PBS was added at 100 µg/well and incubated over night at room temperature. Substrate, in the form of 4 OPD-tablets Dako S2000 dissolved in 12 ml of citric acid buffer, pH 5.0, plus 5 µl of 30% hydrogen peroxide, was then added at 100 µl/well and the absorbance was measured at 450 nm following incubation.

Roughly 600 hybridoma clones were tested. Initially, 190 of these reacted with COLO 205 cells. Of these, 177 reacted also with normal human lymphocytes prepared on Lymphoprep from Nyegaard A/S, Norway, and were discarded. A clone established from one of the remaining clones was designated hybridoma C242 and was isotyped as IgG1 class. The C242 hybridoma was then subjected to a number of subcloning steps to eventually produce a final, stable monoclonal antibody producing a clone designated as C242:II.

Thus, the C242 hybridoma was first cloned resulting in a clone called C242:5. This clone was in turn cloned to form clone C242:5:2. In both these clonings, hybridoma suspension was diluted in hypoxanthine/thymidine (HT) supplemented culture medium to a density of 4 cells/ml. 50 µl (0.2 cells) were distributed to each well in a 96-well culture dish pre-coated with 250 µl of Balb/c mice macrophage suspension ($5 \times 10^3$ macrophages/well) in HT supplemented medium. After 2–5 days, single cell clones were detected by visual inspection in a microscope. On day 6, medium was changed and aliquots of spent media analyzed for quantity of antibodies binding to COLO 205 cells but not to normal human cells by ELISA as described above. The best clones in terms of positive reaction in the COLO 205 ELISA with retained negative reaction in the normal cell ELISA were selected and frozen in vials in liquid nitrogen for further development.

For performing a third cloning, the cells were thawed and cultured in DMEM (Dulbecco's Modified Eagle's Medium) (5% FCS). Cells were then seeded into the wells of a 96-well tissue culture plate at a mean density of three cells per well. The cloning was performed in DMEM with 5% FCS and mouse macrophages used as feeder cells. On this plate, 30 clones occurred of which 16 were tested for IgG production by nephelometry and specificity of the antibodies by ELISA as described above. Twelve of these clones were found to produce IgG. Ten clones were then expanded on a 24-well tissue culture plate from which spent medium was tested for IgG production and specificity. This selection resulted in the saving of 4 clones with relatively high productivity. A final productivity test of these four clones was performed in duplicate tissue culture flasks. The clone showing the highest productivity was selected and designated as C242/CL 510 A1. It was frozen in liquid nitrogen for further use.

A first cloning of the clone C242/CL 510 A1 indicated that one third of the cells did not produce IgG as judged by an absorbance of less than 0.1 at a dilution of 1:1000 in a general mouse IgG ELISA. Five positive subclones were pooled to create a clone called C242:I. The productivity from this clone was quantified by a general HPLC-based assay to be 150 µg of mouse IgG per ml.

Clone C242:I was subsequently cloned into a 96-well dish yielding 33 clones, all positive for mouse IgG production. Five of these, all yielding above 150 µg/ml, were pooled to create a final clone, designated as C242:II, having a stable productivity of IgG. HPLC assay indicated the productivity of C242:II to be 196 µg of mouse IgG per ml. The cells were frozen and stored in vials in liquid nitrogen. A sample of the C242:II hybridoma produced was deposited at the ECACC under accession number 90012601 as stated above.

Production of C242:II monoclonal antibody

An initial cell suspension of the above prepared hybridoma was obtained from a frozen vial. Cells were seeded into tissue culture chambers with a total area of 6000 cm$^2$ from Nunc A/S at a density of $2 \times 10^4$ cells/ml (C242:II hybridoma). The cells were then cultured in DMEM modified according to Iscove (Iscove N. N., and Melchers F., J. Exp. Med. vol. 147, p 923 (1978) and supplemented with 1% gentamycin, 1% amino-acid supplement and 5% fetal calf serum. The cells were then incubated for 4 or 5 days at 37° C. in a humidified atmosphere containing 8% $CO_2$. At the end of incubation cells were counted and samples were taken for determination of monoclonal antibody concentration. The cell culture supernatant was decanted and filtered through a cellulose filter in order to remove suspended cells. The supernatant was then concentrated 20–30 times by ultrafiltration in a Millipore Pellican Ultrafiltration cell using a 30,000 molecular weight cut-off membrane. A sample from the concentrate was taken for analysis of C242:II monoclonal antibody concentration and antigen reactivity, whereupon the monoclonal antibody concentrate was stored at −70° C. until purification.

Purification of C242:II monoclonal antibody

Protein-A-Sepharose® 4B (Pharmacia AB, Uppsala, Sweden) was prepared according to the manufacturer's instructions concerning swelling and washing of the gel, whereupon the above produced C242:II antibody concentrate was bound thereto using 1.5M glycine-NaOH, 3M NaCl, pH 8.9, as binding buffer. After an initial washing using the same buffer, the affinity column was eluted with 0.1M citric acid-NaOH, pH 5.0, and the C242:II monoclonal antibody was collected in tubes containing 1 mole/l of Tris-HCl, pH 8.0. The antibody obtained was then dialyzed against 0.02M phosphate buffer, 0.15M NaCl, pH 7.2, 0.2 g/l $NaN_3$. The dialyzed C242:II antibody was then concentrated by ultrafiltration using a 30,000 molecular weight cut-off membrane. After taking of samples for concentration and quality control analysis the C242:II monoclonal was stored at −20° C.

EXAMPLE 2

Immunohistochemical evaluation of C242:II in colorectal cancer and normal tissues Specimens from primary colo-rectal carcinoma and various normal tissues were obtained from patients undergoing surgical resection. The tissues were kept on ice and were frozen within 1 hour after resection in iso-pentane pre-chilled with liquid nitrogen. The tissues were stored at −70° C. until sectioned. The frozen biopsies were cut into 5 µm sections and fixed in 50% acetone for 30 seconds at +4° C. followed by 100% acetone for 5 minutes at +4° C. The sections were air-dried and rinsed in PBS for 10 minutes. All sections were then incubated in 0.3% hydrogen peroxide in PBS for 5 minutes to block endogenous peroxidase and rinsed twice in PBS. Thereafter the sections were treated with normal swine serum and diluted 1:10 in PBS-4% BSA for 5 minutes at +4° C. to block non-specific binding of antibodies.

All incubations with antibodies were carried out in a humid atmosphere for 30 minutes at room temperature. The sections were first incubated with monoclonal antibody C242:II, obtained in Example 1 above, in PBS-4% BSA, thereafter with biotinylated horse anti-mouse IgG (Vectastain™, Vector Laboratories Burlingame, Calif., U.S.A.) diluted 1:400 in PBS-4% BSA with 2% swine anti-rabbit immunoglobulin and finally with Avidin DH/biotinylated horseradish peroxidase H complex (Dakopatts A/S, Copenhagen, Denmark). After each incubation the slides were rinsed in PBS for 15 minutes. The sections were then treated with substrate for 15 minutes, rinsed in PBS, counterstained with haematoxylin and mounted with glycerol-gelatin (Merck, Darmstadt, Germany). The substrate used was 10 mg of 3-amino-9-ethylcarbazole (Sigma, St. Louis, Mo., U.S.A.) dissolved in 6 ml of dimethylsulfoxide and diluted with 50 ml of 0.02M sodium acetate, pH 5.5, containing 4 µl of 30% $H_2O_2$. The substrate solution was filtered prior to use. The sections were then examined and the results are presented in Table 1 below.

TABLE 1

| Staining of colo-rectal tumours and various normal tissues with C242:II | |
|---|---|
| TISSUE | STAINED/TOTAL |
| Colo-rectal carcinoma | 26/41 |
| Normal colon | 8/16 |
| mammary gland | 2/3 |
| parotid gland | 2/2 |

TABLE 1-continued

Staining of colo-rectal tumours
and various normal tissues with C242:II

| TISSUE | STAINED/TOTAL | |
| --- | --- | --- |
| skin | 0/1 | slight staining of sweat glands |
| liver ducts | 0/2 | weak staining of bile |
| kidney | 0/1 | |
| pancreas | 2/2 | ducts |
| stomach | 0/1 | |
| small intestine | 0/1 | |

As appears from Table 1, 63% of the examined biopsies from colo-rectal tumours showed positive staining with monoclonal C242:II. The expression of the antigen CA242 in normal colonic tissue was found to be generally weaker than in tumour tissue, the staining being entirely localized to columnar epithelium and goblet cells. Non-colon normal tissue was almost devoid of reactivity with monoclonal C242:II, whereas positivity was found in normal breast ducts, pancreatic ducts, bile ducts, and sweat glands, but the intensity of staining was weak.

EXAMPLE 3

Endocytosis of C242:II binding to COLO 205 human colon carcinoma

An endocytosis assay was conducted as follows: Single cell suspensions were prepared from COLO 205 cells (see Example 1) grown as a monolayer culture. The cells were trypsinized, extensively washed and resuspended in culture medium. Iodine labelled C242:II antibody from Example 1 (200 000 cpm corresponding to 50 ng of monoclonal antibody) was added to a single cell suspension of COLO 205 cells ($10^6$ cells) in 5 ml test tubes. The final volume was 200 μl/tube.

Cells were incubated in the presence of $^{125}$I-C242 for 1 hour on ice (0° C.). The suspension was then centrifuged and the cells were washed free from unbound monoclonal antibody. The preincubated cells were further incubated at 37° C. for 10 minutes time intervals during 1 hour, the cells being rechilled and pelleted at each time. Radiolabel released to the culture medium was measured from the supernatant (LKB gamma counter, Pharmacia AB, Uppsala, Sweden). The supernatant was also subjected to TCA precipitation and the radioactivity of the precipitate was measured. Surface bound $^{125}$I-C242 was removed by acid wash with 0.2M glycine-HCl buffer, pH 1.5, containing 2.5 mg/ml papain, and the radioactivity, representing internalized $^{125}$I-C242, was counted. The amount of surface bound antibody after each time, incubated at 37° C., was calculated by subtracting released and internalized monoclonal antibody from total surface bound monoclonal antibody. Degradation of released antibody was measured from TCA precipitation of medium supernatant.

The results are presented in FIG. 1 in the accompanying drawing showing the endocytosis of $^{125}$I-C242:II by COLO 205 cells, the radioactivity on cell surface ("Sur"), internalized radioactivity ("Int"), released radioactivity ("Res") and degraded released radioactivity ("Deg.Re") being expressed as the percentage of total initial radioactivity on cell surface. In FIG. 1 it can be seen that a more than 20% internalization of C242:II was obtained within 1 hour when preincubated cells were incubated at 37° C. There were small amounts of acid soluble radioactivity when medium supernatant was TCA precipitated which indicates little fragmentation of released activity after 1 hour of incubation.

EXAMPLE 4

Molecular cloning of cDNA's encoding parts of the light and heavy chains of the monoclonal antibody C242:II A. Preparation of total RNA Total RNA from $10^8$ cells was prepared essentially according to the method of Chirgwin, J. M. et al. (1979; Biochemistry 18, 5294–5299) as modified by Chomezynksi, P. and Sacchi, N, (1987; Anal. Biochem. 162, 156–159). Briefly, the cell pellet was dissolved in 15 ml of cold denaturing solution consisting of 4M guanidinium thiocyanate; 25 mM sodium citrate, pH 7; 0.5% N-lauroyl sarcosine; 0.1M 2 mercaptoethanol. After the dissolution of the cell material 1.2 ml of 2M sodium acetate (pH 4.0) was added and the mixture extracted with phenol-chloroformisoamyl alcohol (250:49:1). After centrifugation the RNA was precipitated from the aqueous phase by adding an equal volume of isopropanol, and incubating at –20° C. over night in order to precipitate the total RNA. After centrifugation and resuspension of the RNA, the precipitation was repeated, and after an additional centrifugation and precipitation the total RNA yield was calculated to be 960 μg based on absorbance measurements.

B. Isolation of mRNA

In order to isolate polyadenylated mRNA from the above preparation of total RNA, the PolyATract™ mRNA isolation system of Promega Corporation, Madison, Wis., U.S.A., was utilized according to the manufacturer's instructions (c.f.: Promega Technical Bullentin, No. 090: 1990). Briefly, 960 μg of total RNA were dissolved in water and annealed with a biotinylated oligo(dT) probe (50 pmoles) in 0.4×SSC (1×SSC=8.77 g NaCl, 4.41 g sodium citrate per liter of water at pH 7.0). Streptavidin coated paramagnetic beads (Streptavidin Magnesphere™) were added and after a 10 min. incubation the magnetic particles were removed and washed several times with 0.1×SSC. The polyadenylated mRNA was eluted from the spheres by incubation in water, yielding 5 μg of mRNA.

C. Preparation of cDNA phage library in *E. coli* cDNA was prepared from polyadenylated mRNA of the previous step essentially according to the method of Gubler, U., and Hoffman, B. J. (1983; Gene 25, 263–269), as modified for the vector Uni-ZAP™ (Stratagene Inc. La Jolla, Calif.) which permits unidirectional cloning of double stranded cDNA. Briefly, 5 μg of polyadenylated mRNA was converted to single stranded cDNA by priming with the Uni-ZAP™ linker primer (56 ng/ml), adding dATP, dGTP, dTTP, and 5-methyl-dCTP, at 0.6 mM, and 45 U of Moloncy Murine Leukemia Virus reverse transcriptase. The mixture was incubated at 37° C. for 1 hours. Second strand cDNA synthesis was performed by adding dATP, dGTP, dTTP, and dCTP to a final concentration of 0.15 mM, 3.2 U RNase H, and 6.5 U DNA Polymerase 1, and incubating for 2.5 hours at 16° C. The mixture was extracted with phenol-chloroform (1:1) and ethanol precipitated. The ends of the cDNA were rendered blunt by incubating with 0.16 mM dNTP and 10 U T4 DNA polymerase at 37° C. for 30 min. After phenol-chloroform extraction and ethanol precipitation, the resulting blunt-ended cDNA was ligated to EcoRI adaptors by adding 3 Weiss U T4 DNA ligase, 1 mM ATP, and incubating over night at 8° C. After ligation the EcoRI cohesive ends were kinased by adding 10 U T4 Polynucleotide kinase in the presence of 1 mM ATP, and incubating for 30 minutes at 37° C. The resulting cDNA with phosphorylated EcoRI cohesive ends, was digested with 90 U XhoI in order to create an XhoI cohesive end from the sequence encoded by the Uni-ZAP™ linker primer. The resulting cDNA was then ligated to 1 μg of Uni-ZAP™ XR EcoRI and XhoI prepared arms in the presence of 2 Weiss U T4 DNA ligase, 1 mM ATP, and incubating at 12° C. overnight. The ligation mixture was packed in vitro into—phage particles by using the Gigapack II Gold® packaging extract according to the manufacturer's instructions, and the resulting phages were used to infect E. coli PLK-F'. the resulting cDNA library of $8.5 \times 10^4$ independent clones was amplified once to give a phage titer of $7.5 \times 10^8$ pfu/ml. The resulting cDNA library was screened using E. coli XL1-Blue as host strain (c.f. Bullock. W. (1978) Biotechniques 5, 4) as will be described below.

D. Preparation of hybridization probes

In order to detect cDNA clones encoding the IgG1 heavy chain and kappa chain of the C242:II antibody, hybridization probes covering the first constant domain of the heavy chain, CH1, and the constant domain of the kappa chain, CK, were prepared from mouse genomic DNA by the polymerase chain reaction according to Saiki. R. H., et al. (1988; Science 239, 487–491). Briefly, oligonucleotide primer pairs hybridizing to the 5' and 3' regions of the exons encoding the above immunoglobulin domains were used for amplification of mouse genomic DNA. After purification by agarose gel electrophoresis the resulting DNA probe fragments were labeled with $^{32}P$ by the random primer extension method according to Feinberg, A. P., and Vogelstein, B. (1983; Anal. Biochem. 132, 6).

E. Screening for IgG1 heavy and kappa chains encoding sequences and insertion into plasmids The cDNA library from section C above was screened in two separate rounds using the immunoglobulin IgG1 and kappa probes, respectively, from section D according to methods described by Sambrook, J. et al. (1989; Molecular Cloning, 2nd Ed, Cold Spring Harbor Laboratory Press). Positively hybridizing phage clones from the two separate hybridisations were further purified by rescreening using the same probes as in the initial screening. Positively hybridizing phage clones were expanded in cultures of E. coli XL1-Blue, and the resulting phage stocks used to prepare cDNA containing pBluescript SK(−) plasmids by phagemid excision and propagation essentially according to Short, J. M. et al. (1988; Nucleic Acids Res. 16, 7583–7600).

F. Characterization of plasmid cDNA from hybridizing colonies

The resulting cDNA containing plasmids were characterised by restricion enzyme mapping, and plasmids containing inserts of the expected sizes were subjected to dideoxy DNA sequencing according to Sanger, F. et al. (1977; Proc. Natl. Acad. Sci. USA 74, 5463–5467). A plasmid hybridizing with the Ig kappa probe, denoted pKGE761, contained a cDNA insert whose sequence encodes an open reading frame closely homologous to previously known mouse kappa light chain sequences (c.f. Kabat, E. A. et al. (1987) Sequences of Protein of Immunological Interest, 4th Ed., U.S. Department of Health and Human Services, National Institutes of Health). A partial cDNA sequence encoding the variable region of the kappa light chain, VK, and its translated protein sequence, is depicted in FIG. 3. The three CDR sequences, designated as CDR1 to CDR3, are indicated by underlining. A signal peptide preceding the aminoterminal end of the VK segment is indicated by S. CK indicates the constant region following the carboxyterminal end of the VK sequence.

A plasmid hybridizing with the IgG1 probe, denoted pKGE762, contained a cDNA insert whose sequence encodes and open reading frame closely homologous to previously known mouse IgG1 heavy chain sequences (c.f. Kabat, E. A., et al. vide supra). A partial cDNA sequence encoding the IgG1 heavy chain variable region, VH, and its translated protein sequence, is depicted in FIG. 4. The three CDR sequences, designated as CDR1 to CDR3, are indicated by underlining. A signal peptide preceding the aminoterminal end of the VH segment is indicated by S. CH1 indicates the constant region following the carboxyterminal end of the VH sequence.

We claim:

1. A substantially pure antibody which binds the same epitope as the antibody produced by hybridoma cell line C242:II, which cell line has ECACC identification number 90012601.

2. An antibody according to claim 1, wherein said antibody is produced by hybridoma cell line C242:II, which cell line has ECACC identification number 90012601.

3. An antibody according to claim 1, wherein the antibody is an antigen binding fragment.

4. An antibody according to claim 2, wherein the antibody is an antigen binding fragment.

5. A substantially pure antibody according to claim 1, which antibody having the binding characteristics to bind specifically to the same epitope as an antibody that has in its complementary determining regions (CDR)

(a) in its Kappa Chain
      CDR1: a polypeptide having the a sequence according to SEQ ID NO:1:,
      CDR2: a polypeptide having the a sequence according to SEQ ID NO:2:, and
      CDR3: a polypeptide having the a sequence according to SEQ ID NO:3:, and
   (b) in its Heavy Chain
      CDR1: a polypeptide having the a sequence according to SEQ ID NO:4:,
      CDR2: a polypeptide having the a sequence according to SEQ ID NO:5:, and
      CDR3: a polypeptide having the a sequence according to SEQ ID NO:6:.

6. A substantially pure antibody according to claim 1, which antibody having the binding characteristics to bind specifically to the same epitope as an antibody that has in its complementary determining regions (CDR)

(a) in its Kappa Chain
      CDR1: a polypeptide having the a sequence according to SEQ ID NO:9,
      CDR2: a polypeptide having the a sequence according to SEQ ID NO:10:, and
      CDR3: a polypeptide having the a sequence according to SEQ ID NO: 11: and
   (b) in its Heavy Chain
      CDR1: a polypeptide having the a sequence according to SEQ ID NO:12:,
      CDR2: a polypeptide having the a sequence according to SEQ ID NO:13:, and
      CDR3: a polypeptide having the a sequence according to SEQ ID NO:14:.

7. A method for diagnosing a tumor antigen in vitro, comprising the steps of contacting a sample with a monoclonal antibody according to claim 1 under conditions permitting formation of a complex containing said monoclonal antibody bound to its antigen and subsequently determining that the complex formed, the amount of which is correlated to the amount of antigen present in the sample.

8. A cell line capable of producing the antibody according to claim 1.

9. A cell line according to claim 8, which is a hybridoma cell line C242:II with ECACC identification number 900012601.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 16
        ( B ) TYPE: amino acid
        ( C ) STRANDEDNESS: single
        ( D ) TOPOLOGY: linear ( i i ) MOLECULE TYPE: Polypeptide ( x i ) SEQUENCE DESCRIPTION: SEQ ID NO:1:

Arg  Ser  Ser  Lys  Ser  Leu  Leu  His  Ser  Asn  Gly  Asn  Thr  Tyr  Leu  Tyr
1                   5                        10                            15

( 2 ) INFORMATION FOR SEQ ID NO:2:

( i ) SEQUENCE CHARACTERISTICS:
        ( A ) LENGTH: 7

(B) TYPE: amino acid
                    (C) STRANDEDNESS: single
                    (D) TOPOLOGY: linear (ii) MOLECULE TYPE: Polypeptide (xi) SEQUENCE DESCRIPTION: SEQ ID NO:2:

Arg Met Ser Asn Leu Val Ser
 1               5

(2) INFORMATION FOR SEQ ID NO:3:

(i) SEQUENCE CHARACTERISTICS:
                    (A) LENGTH: 9
                    (B) TYPE: amino acid
                    (C) STRANDEDNESS: single
                    (D) TOPOLOGY: linear (ii) MOLECULE TYPE: Polypeptide (xi) SEQUENCE DESCRIPTION: SEQ ID NO:3:

Leu Gln His Leu Glu Tyr Pro Phe Thr
 1               5

(2) INFORMATION FOR SEQ ID NO:4:

(i) SEQUENCE CHARACTERISTICS:
                    (A) LENGTH: 5
                    (B) TYPE: amino acid
                    (C) STRANDEDNESS: single
                    (D) TOPOLOGY: linear (ii) MOLECULE TYPE: Polypeptide (xi) SEQUENCE DESCRIPTION: SEQ ID NO:4:

Tyr Tyr Gly Met Asn
 1               5

(2) INFORMATION FOR SEQ ID NO:5:

(i) SEQUENCE CHARACTERISTICS:
                    (A) LENGTH: 17
                    (B) TYPE: amino acid
                    (C) STRANDEDNESS: single
                    (D) TOPOLOGY: linear (ii) MOLECULE TYPE: Polypeptide (xi) SEQUENCE DESCRIPTION: SEQ ID NO:5:

Trp Ile Asp Thr Thr Thr Gly Glu Pro Thr Tyr Ala Glu Asp Phe Lys
 1               5                  10                  15
Gly (2) INFORMATION FOR SEQ ID NO:6:

(i) SEQUENCE CHARACTERISTICS:
                    (A) LENGTH: 10
                    (B) TYPE: amino acid
                    (C) STRANDEDNESS: single
                    (D) TOPOLOGY: linear (ii) MOLECULE TYPE: Polypeptide (xi) SEQUENCE DESCRIPTION: SEQ ID NO:6:

Arg Gly Pro Tyr Asn Trp Tyr Phe Asp Val
 1               5                  10

(2) INFORMATION FOR SEQ ID NO:7:

(i) SEQUENCE CHARACTERISTICS:
  (A) LENGTH: 141
  (B) TYPE: amino acid
  (C) STRANDEDNESS: single
  (D) TOPOLOGY: linear (ii) MOLECULE TYPE: Polypeptide (xi) SEQUENCE DESCRIPTION: SEQ ID NO:7:

```
Met Arg Cys Leu Ala Glu Phe Leu Gly Leu Leu Val Leu Trp Ile Pro
 1               5                  10                  15

Gly Ala Ile Gly Asp Ile Val Met Thr Gln Ala Ala Pro Ser Val Pro
                20                  25                  30

Val Thr Pro Gly Glu Ser Val Ser Ile Ser Cys Arg Ser Ser Lys Ser
            35                  40                  45

Leu Leu His Ser Asn Gly Asn Thr Tyr Leu Tyr Trp Phe Leu Gln Arg
    50                  55                  60

Pro Gly Gln Ser Pro Gln Leu Leu Ile Tyr Arg Met Ser Asn Leu Val
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Leu Gln His Leu Glu Tyr Pro Phe Thr Phe Gly Pro Gly Thr Lys
            115                 120                 125

Leu Glu Leu Lys Arg Ala Asp Ala Ala Pro Thr Val Thr
    130                 135                 140
```

(2) INFORMATION FOR SEQ ID NO:8:

(i) SEQUENCE CHARACTERISTICS:
  (A) LENGTH: 148
  (B) TYPE: amino acid
  (C) STRANDEDNESS: single
  (D) TOPOLOGY: linear (ii) MOLECULE TYPE: Polypeptide (xi) SEQUENCE DESCRIPTION: SEQ ID NO:8:

```
Met Asp Trp Leu Arg Asn Leu Leu Phe Leu Met Ala Ala Ala Gln Ser
 1               5                  10                  15

Ile Gln Ala Gln Val Gln Leu Val Gln Ser Gly Pro Glu Leu Lys Lys
                20                  25                  30

Pro Gly Glu Thr Val Lys Ile Ser Cys Lys Ala Ser Asp Tyr Thr Phe
            35                  40                  45

Thr Tyr Tyr Gly Met Asn Trp Val Lys Gln Ala Pro Gly Lys Gly Leu
    50                  55                  60

Lys Trp Met Gly Trp Ile Asp Thr Thr Thr Gly Glu Pro Thr Tyr Ala
65                  70                  75                  80

Glu Asp Phe Lys Gly Arg Ile Ala Phe Ser Leu Glu Thr Ser Ala Ser
                85                  90                  95

Thr Ala Tyr Leu Gln Ile Lys Asn Leu Lys Asn Glu Asp Thr Ala Thr
            100                 105                 110

Tyr Phe Cys Ala Arg Arg Gly Pro Tyr Asn Trp Tyr Phe Asp Val Trp
            115                 120                 125

Gly Ala Gly Thr Thr Val Thr Val Ser Ser Ala Lys Thr Thr Pro Pro
    130                 135                 140

Ser Val Tyr Pro
145
```

( 2 ) INFORMATION FOR SEQ ID NO:9:

( i ) SEQUENCE CHARACTERISTICS:
        ( A ) LENGTH: 18
        ( B ) TYPE: amino acid
        ( C ) STRANDEDNESS: single
        ( D ) TOPOLOGY: linear ( i i ) MOLECULE TYPE: Polypeptide ( x i ) SEQUENCE DESCRIPTION: SEQ ID NO:9:

```
Arg Ser Ser Lys Ser Leu Leu His Ser Asn Gly Asn Thr Tyr Leu Tyr
 1               5                  10                  15
Trp Phe
```

( 2 ) INFORMATION FOR SEQ ID NO:10:

( i ) SEQUENCE CHARACTERISTICS:
        ( A ) LENGTH: 9
        ( B ) TYPE: amino acid
        ( C ) STRANDEDNESS: single
        ( D ) TOPOLOGY: linear ( i i ) MOLECULE TYPE: Polypeptide ( x i ) SEQUENCE DESCRIPTION: SEQ ID NO:10:

```
Arg Met Ser Asn Leu Val Ser Gly Val
 1               5
```

( 2 ) INFORMATION FOR SEQ ID NO:11:

( i ) SEQUENCE CHARACTERISTICS:
        ( A ) LENGTH: 11
        ( B ) TYPE: amino acid
        ( C ) STRANDEDNESS: single
        ( D ) TOPOLOGY: linear ( i i ) MOLECULE TYPE: Polypeptide ( x i ) SEQUENCE DESCRIPTION: SEQ ID NO:11:

```
Leu Gln His Leu Glu Tyr Pro Phe Thr Phe Gly
 1               5                  10
```

( 2 ) INFORMATION FOR SEQ ID NO:12:

( i ) SEQUENCE CHARACTERISTICS:
        ( A ) LENGTH: 7
        ( B ) TYPE: amino acid
        ( C ) STRANDEDNESS: single
        ( D ) TOPOLOGY: linear ( i i ) MOLECULE TYPE: Polypeptide ( x i ) SEQUENCE DESCRIPTION: SEQ ID NO:12:

```
Phe Thr Tyr Tyr Gly Met Asn
 1               5
```

( 2 ) INFORMATION FOR SEQ ID NO:13:

( i ) SEQUENCE CHARACTERISTICS:
        ( A ) LENGTH: 21
        ( B ) TYPE: amino acid
        ( C ) STRANDEDNESS: single
        ( D ) TOPOLOGY: linear ( i i ) MOLECULE TYPE: Polypeptide ( x i ) SEQUENCE DESCRIPTION: SEQ ID NO:13:

```
Met Gly Trp Ile Asp Thr Thr Thr Gly Glu Pro Thr Tyr Ala Glu Asp
```

```
    1               5                    10                   15
Phe Lys Gly Arg Ile
              20
```

( 2 ) INFORMATION FOR SEQ ID NO:14:

( i ) SEQUENCE CHARACTERISTICS:
        ( A ) LENGTH: 14
        ( B ) TYPE: amino acid
        ( C ) STRANDEDNESS: single
        ( D ) TOPOLOGY: linear ( i i ) MOLECULE TYPE: Polypeptide ( x i ) SEQUENCE DESCRIPTION: SEQ ID NO:14:

```
Arg Arg Arg Gly Pro Tyr Asn Trp Tyr Phe Asp Val Trp Gly
 1               5                    10
```

( 2 ) INFORMATION FOR SEQ ID NO:15:

( i ) SEQUENCE CHARACTERISTICS:
        ( A ) LENGTH: 464 base pairs
        ( B ) TYPE: Nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
GGAATTCGGC ACGAGGAGTT TTTTTGTATC AAGTTCTCAG AATGAGGTGC CTAGCTGAGT      60
TCCTGGGGCT GCTTGTGCTC TGGATCCCTG GAGCCATTGG GGATATTGTG ATGACTCAGG     120
CTGCACCCTC TGTACCTGTC ACTCCTGGAG AGTCAGTATC CATCTCCTGC AGGTCTAGTA     180
AGAGTCTCCT GCATAGTAAT GGCAACACTT ACTTGTATTG GTTCCTGCAG AGGCCAGGCC     240
AGTCTCCTCA GCTCCTGATA TATCGGATGT CCAACCTTGT CTCAGGAGTC CCAGACAGGT     300
TCAGTGGCAG TGGGTCAGGA ACTGCTTTCA CACTGAGAAT CAGTAGAGTG GAGGCTGAGG     360
ATGTGGGTGT TTATTACTGT CTGCAACATC TAGAGTATCC GTTCACGTTC GGTCCTGGGA     420
CCAAGCTGGA GCTGAAACGG GCTGATGCTG CACCAACTGT AACG                     464
```

( 2 ) INFORMATION FOR SEQ ID NO:16:

( i ) SEQUENCE CHARACTERISTICS:
        ( A ) LENGTH: 480 base pairs
        ( B ) TYPE: Nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
GAATTCGGCA CGAGATTGAG CCCAAGTCTT AGACATCATG GATTGGCTGC GGAACTTGCT      60
ATTCCTGATG GCAGCTGCCC AAAGTATCCA AGCACAGGTC CAGTTGGTGC AGTCTGGACC     120
TGAGCTGAAG AAGCCTGGAG AGACAGTCAA GATCTCCTGC AAGGCTTCTG ATTATACCTT     180
CACATACTAT GGAATGAACT GGGTGAAGCA GGCTCCGGGA AAGGGTTTAA AGTGGATGGG     240
CTGGATAGAC ACCACCACTG GAGAGCCAAC ATATGCTGAA GATTTTAAGG ACGGATTGC      300
CTTCTCTTTG GAGACCTCTG CCAGCACTGC CTATTTGCAG ATCAAAAACC TCAAAAATGA     360
GGACACGGCT ACATATTTCT GTGCAAGACG GGGGCCTTAC AACTGGTACT TTGATGTCTG     420
GGGCGCAGGG ACCACGGTCA CCGTCTCCTC AGCCAAAACG ACGCCCCCAT CTGTCTATCC     480
```